United States Patent [19]
Leung et al.

[11] Patent Number: 6,002,066
[45] Date of Patent: Dec. 14, 1999

[54] H2-M MODIFIED TRANSGENIC MICE

[75] Inventors: Wai-Ping Leung, San Diego; Lars Karlsson, La Jolla, both of Calif.; Lubing Zhou, East Brunswick, N.J.; Per A. Peterson, Rancho Sante Fe, Calif.

[73] Assignee: Ortho Pharmaceutical Corp., Raritan, N.J.

[21] Appl. No.: 08/780,949

[22] Filed: Jan. 10, 1997

Related U.S. Application Data

[60] Provisional application No. 60/009,917, Jan. 16, 1996.

[51] Int. Cl.$^6$ ............ C12N 15/09; C12N 15/63; C12N 15/00; C12N 5/00
[52] U.S. Cl. ............... 800/18; 800/21; 800/22; 800/25; 800/11; 800/3; 435/455; 435/463; 435/320.1; 435/325; 435/69.1; 435/91.2; 435/4; 424/9.21
[58] Field of Search ............... 800/2, 18, 21, 800/22, 25, 11, 3; 435/172.3, 325, 320.1, 69.1, 91.2, 4, 455, 463; 424/9.2, 9.21

[56] References Cited

PUBLICATIONS

Bradley et al., Biotechnology, vol. 10, pp. 534–539,. May 1992.
Seamark, Reproduction, Fertility and Development, vol. 6, pp. 653–657, 1994.
Mullins et al., Journal of Clinical Investigations, vol. 98, pp. S37–S40, 1996.
Capecchi, Scientific American, vol. 270, pp. 34–41, Mar. 1994.
Hermel et al., Immunogenetics, vol. 42, pp. 136–142, 1995.
Cho et al., Nature, vol. 353, pp. 573–576, Abstract only, 1991.
Grusby et al., Science, vol. 253, pp. 1417–1420, Sep. 20, 1991.
Grusby et al., Annual Review of Immunology, vol. 13, pp. 417–435, 1995.
Denzin et al., Immunity, vol. 1, pp. 595–606,. Oct. 1, 1994.
H2–M Mutant Mice Are Defective in The Peptide Loading of Class II Molecules, Antigen Presentation, and T Cell Repertoire Selection, W. David Martin, Cell, vol. 84, 543–550, Feb. 23, 1996.
Mice Lacking H2–M Complexes, Enigmatic Elements of the MHC Class II Peptide–Loading Pathway, Toru Miyazaki, Cell, vol. 84, 531–541, Feb. 23, 1996.
Role of The Thrombin Receptor in Development and Evidence for a Second Receptor, Andrew J. Connolly, Nature, vol. 381, 516–519, Jun. 6, 1996.
Amplified RNA Synthesized from Limited Quantities of Heterogeneous cDNA, Russell N. Van Gelder, Proc. Natl. Acad. USA, vol. 87, 1663–1667, Mar. 1990.
Antigen Presentation and T Cell Development in H2–M–Deficient Mice, Wai–Ping Fung–Leung, Science, vol. 271, 1278–1281, Mar. 1,1996.

*Primary Examiner*—Bruce R. Campell
*Assistant Examiner*—Jill D. Martin
*Attorney, Agent, or Firm*—John W. Wallen III

[57] ABSTRACT

A transgenic mouse with alterations in the H2-Ma gene is prepared by introduction of an altered H2-Ma gene into a host mouse. The resulting transgenic mice do not produce functional H2-M molecules.

8 Claims, 12 Drawing Sheets

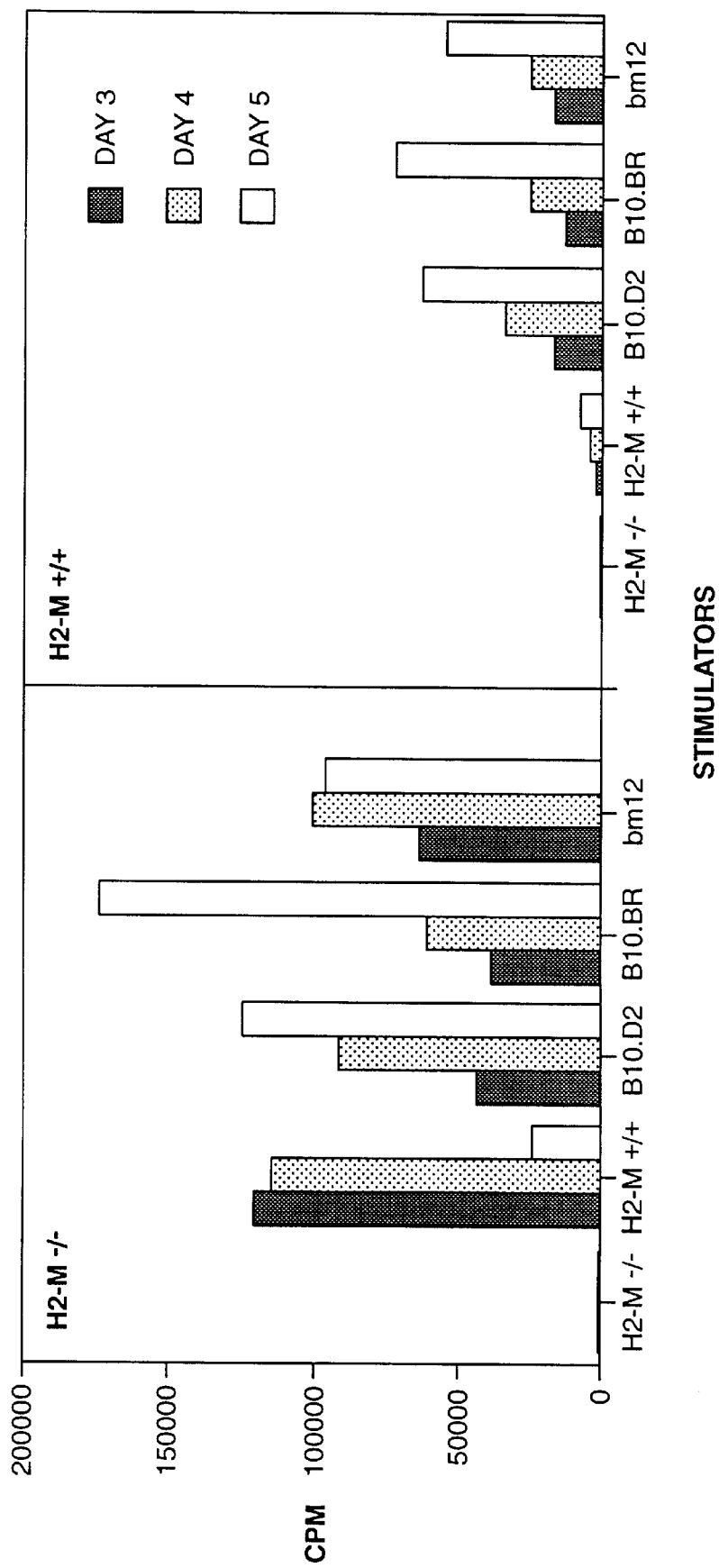

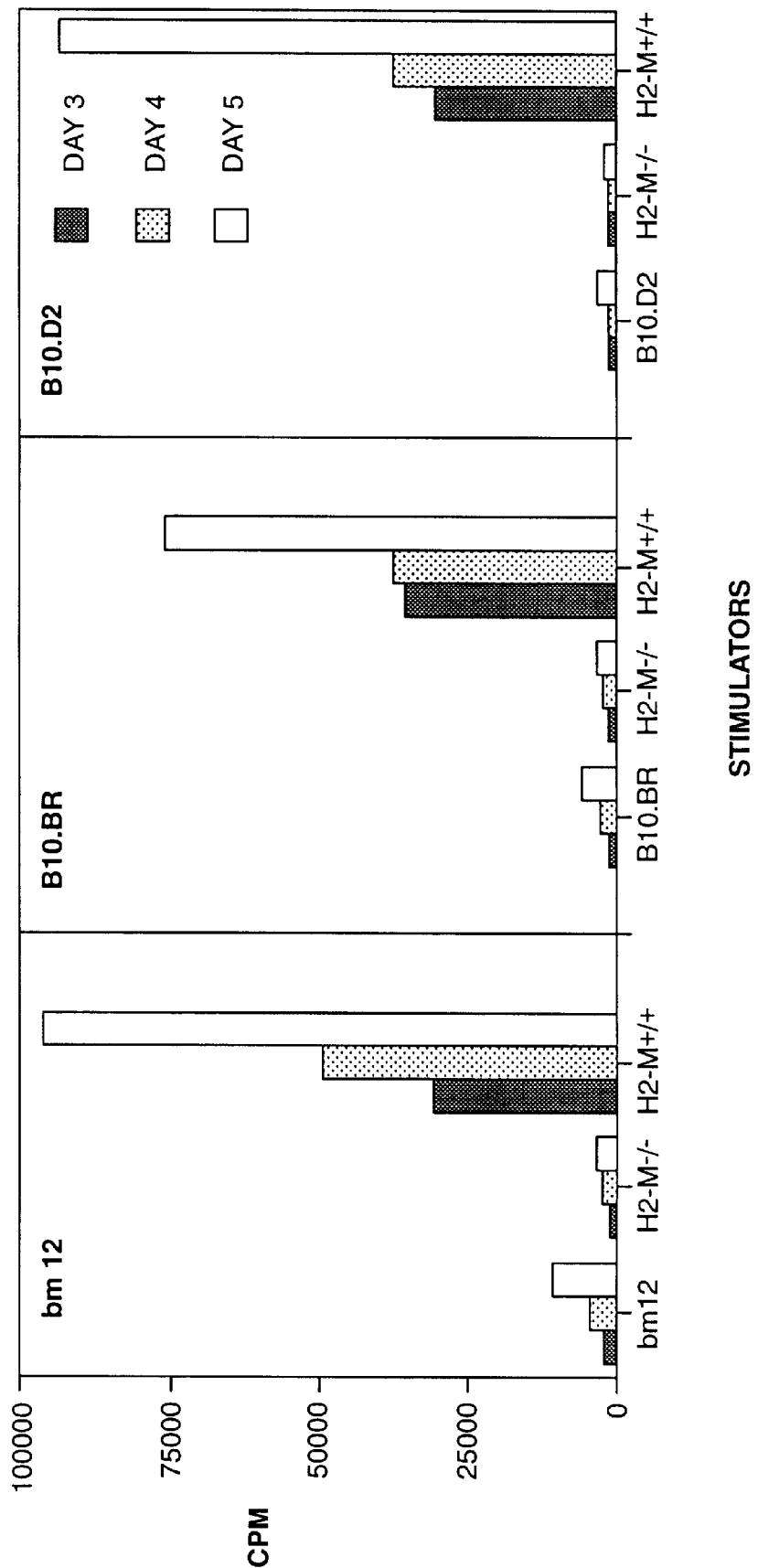

H2-M MODIFIED TRANSGENIC MICE

RELATED APPLICATIONS

This application claims the benefit of U.S. Provisional application Ser. No. 60/009,917, filed on Jan. 16, 1996.

FIELD OF THE INVENTION

The present invention relates to transgenic nonhuman animals wherein the H2-Ma gene is altered, producing an animal lacking functional H2-M.

BACKGROUND OF THE INVENTION

The precise roles of H2-M in the immune system, in normal tissue development and maintenance, as well as in embryonal and fetal development, are not well known at this time. Due to the known involvement of H2-M in the presentation of exogenous antigenic peptides on major histocompatibility complex (MHC) class II molecules, H2-M proteins are important drug targets for modulation of immune responses.

The generation of H2-M modified transgenic animals would aid in defining the biological role(s) of H2-M, and produce an animal model of H2-M deficiency to be used in the design and assessment of chemical and biological approaches to modulating H2-M activity. Such H2-M modified transgenic animals can also be used as a source of cells for cell culture.

The function of MHC class II molecules is to present foreign antigens to T lymphocytes. MHC class II molecules at the cell surface are trimeric complexes of the alpha and beta chains associated with peptides derived from degraded proteins. During infection, the peptides are derived from the invading organisms leading to antigen-specific activation of T lymphocytes. T lymphocytes are also activated by non-self MHC class II molecules which is the basis of graft rejection.

MHC class II molecules are expressed mainly in antigen presenting cells which are derived from the bone marrow. There are three human MHC class II molecules, HLA-DP, HLA-DQ and HLA-DR, while the mouse has two MHC class II molecules, H2-A and H2-E. The process of antigen degradation and peptide association with MHC class II occurrs in the endosomal system of the antigen presenting cells. Intracellularly MHC class II molecules are associated with a third chain, the invariant chain. The invariant chain has several functions; it blocks binding of peptides and proteins to MHC class II in the endoplasmic reticulum (ER); it facilitates MHC class II transport out of the ER; and it directs MHC class II to endosomes where peptide loading occurs. Before peptide loading of MHC class II can occur the invariant chain has to be removed. Proteolysis and acidic pH leads to degradation and removal of most of the invariant chain, but a final fragment, called CLIP (class II-associated invariant chain peptides) cannot be removed by proteolysis, and exchange of this fragment for antigenic peptides is catalyzed by HLA-DM (in human, H2-M in mouse), which is an endosomal or lysosomal resident in MHC class II expressing cells. Cell lines lacking functional HLA-DM can only poorly process and present antigens and instead the MHC II molecules at the cell surface of these cell lines contain the CLIP peptide (Fling et al., 1994, HLA-DMA and -DMB genes are both required for MHC class EIpeptide complex formation in antigen-presenting cells. Nature 368, 554–8; Morris et al., 1994, An essential role for HLA-DM in antigen presentation by class II major histocompatibility molecules. Nature 368, 551–4). Reintroduction of HLA-DM into these cells restores the ability to process antigens showing that HLA-DM is important for modulating the peptide content of MHC class II molecules. Ln vitro experiments have shown that purified HLA-DM can directly mediate peptide exchange in purified MHC class II molecules, leading to exchange of CLIP or other poorly fitting peptides for well fitting peptides (Denzin and Cresswell, 1995, HLA-DM induces CLIP dissociation from MHC class II ad dimers and facilitates peptide loading. Cell 82, 155–165; Sloan et al., 1995, Mediation by HLA-DM of dissociation of peptides from HLA-DR. Nature 375, 802–806). The murine molecule, H2-M, can substitute for HLA-DM in human cell lines and in vitro, but no murine cell lines defective in H2-M have yet been published (Karlsson et al., 1994, Reconstitution of an operational MHC class II compartment in nonantigen-presenting cells. Science 266, 1569–1573; Morris et al., 1994, supra).

MHC class I and class II molecules are essential for the function of the immune system, since activation of T cells requires either one of the two classes of MHC molecules. In a normal situation, the immune system provides good protection against infectious agents and probably against tumor development. However, many pathological states also result from undesirable immune responses. Autoimmune diseases such as rheumatoid arthitis and systemic lupus erythematosus are typical examples of the self attacks by the deregulated immune system that lead to chronic inflammation and eventually the loss of function of the target organs. Rejection of grafts is another example of undesirable reactivity of the immune system in transplantation.

The present treatment options for chronic inflammatory disease are directed towards minimizing the effects of the inflammatory reaction. For severe cases such as organ transplantations, patients are treated with immunosuppressive drugs. These drugs are non-specific, however, since most reactivity of the immune system is decreased and the treated patients become susceptible to all kinds of infections. Many autoimmune diseases are associated with particular MHC class II alleles, although it is unclear exactly how this association is correlated with MHC class II-mediated antigen presentation. It is likely that the ability to modulate only MHC class II-mediated T cell activation could control most of the unwanted immune reactivity, while still leaving protection against infection through MHC class I-restricted T lymphocytes.

SUMMARY OF THE INVENTION

Mice that do not have functional H2-M have been generated and are disclosed herein. These mice provide a valuable animal model to understand the function of H2-M and to evaluate the therapeutic effects of drugs that modulate the function or the expression of HLA-DM in human cells.

BRIEF DESCRIPTION OF THE DRAWINGS

Figure Panels A, B, C, D, and E. Disruption of the mouse H2-Ma gene. (A) Map showing the organization of the H2-Ma gene before (top) and after (bottom) homologous recombination with the targeting construct (middle). A 6.7 kb DNA fragment from a 129/Sv mouse genomic clone covering most of the H2-Ma gene except exon 1 and part of intron 1 was used in the targeting construct as a homologous region for recombination. A cassette containing a neomycin resistance gene (neo) was cloned into the second HindIII site in exon 2 of the H2-Ma gene. A deletion of 61 bp 5' to the neo cassette insertion site in exon 2 was also made in the construct. A herpes simplex thymidine kinase (tk) gene was placed at the 3' end of the construct. Restriction sites are Apa I (A), Hind mII (H), Not I (N), Stu I (S), and Sfi I (Sf). Numbered solid boxes are exons. Location of the probe used in Southern hybridization is shown. (B) Genomic Southern analysis of Apa I digested tail DNA from wild-type (+/+), heterozygous (+/−), and homozygous (−/−) mice for the disrupted H2-Ma gene. The DNA size is 2.8 kb from the endogenous allele and 1.8 kb from the disrupted allele. (C and D) Confocal images of H2-M+/+ (C) or H2-M−/− (D) splenocytes stained with K553 (anti-H2-M)(red) (Karlsson et al., 1994, Resconstitution of an operational MHC class II compartment in nonantigen-presenting cells. Science 266, 1569–1573) and M5/114 (anti-H-2A$^d$) (green) (Bhattacharya et al., 1981, J. Immunol. 127, 2488). K553 staining is present in vesicular structures in C, but absent in D. M5/114 staining is located both at the cell surface and intracellularly in both cases. (E) Immunoprecipitation from $^{35}$S-labeled spleen cells. H2-M+/+ (top) or H2-M−/− (bottom) splenocytes were labeled with $^{35}$S-cysteine as described (Karlsson et al.,1994. Science 266, 1569–1573) for 3 hours before lysis in 1% Triton X-100, PBS, and complete proteinase inhibitor cocktail (Boehringer Mannheim). H2-M was immunoprecipitated with mAb 2E5A, which is reactive with H2-M αβ dimers. Immunoprecipitates were harvested with protein G-sepharose, washed, and resuspended in isoelectric focusing sample buffer. Samples were analyzed by two-dimensional gel electrophoresis, Samples were separated on 7.5 to 12.5% polyacrylamide gels after IEF (pH5 to 7). The gels were then fixed, dried, and autoradiographed. Autoradiographs were scanned with an Agfa ArcusII scanner. Composites were printed on a Kodak XLS 8600 printer. Abbreviations are as follows: α, actin; α, H2-Ma; β, H2-Mb. Acidic proteins are located to the right.

FIG. 4 Panels A, and B. CD4+ T cell fimction and antigen presenting capacity. (A) Reactivity of CD4+T cells from H2-M−/− (left) or H2-M+/+ (right) mice to APCs from different mouse strains. (B) Ability of H2-M−/− and H2-M+/+ APCs to stimulate allogeneic CD4+ T cells. Responses were analyzed after 3, 4 and 5 days of culture. Responder cell populations were pooled lymph node cells enriched for CD4+ cells by treatment with a cocktail of antibodies specific for B cells, MHC class II-expressing cells, and CD8$^+$ cells as described (Webb and Sprent, 1990. Science 248, 1643) together with complement. Spleen cells depleted of T cells by treatment with antibody to CD4 (RL172), anti-CD8 (3.16.8), anti-Thy-i (J1J), and complement were treated with mitomycin C and used as a source of APCs. Responder cells (1.5×10$^5$) were cultured with 5×10$^5$ APCs in a final volume of 200 μl of $^3$H-thymidine for approximately 18 hours before harvesting and counting.

DETAILED DESCRIPTION OF THE INVENTION

Figure 1A:
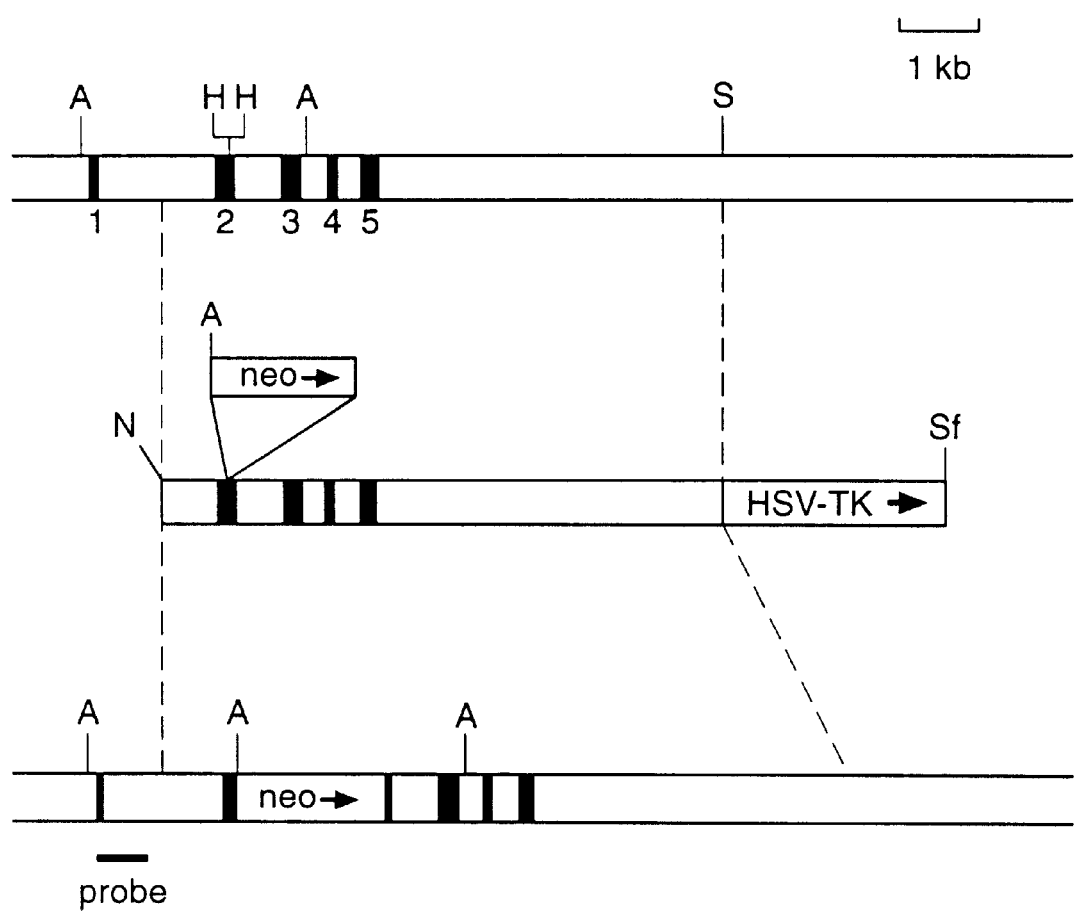

H2-M expressed in mice is composed of the alpha (H2-Ma) and beta (H2-Mb) chains. The alpha chain is encoded by a single copy gene named the H2-Ma gene, whereas the beta chain can be the product of either the H2-Mb1 or H2-Mb2 genes which are highly homologous and chromasomally located next to each other (Cho et al., 1991, A cluster of transcribed sequences between the Pb and Ob genes of the murine major histocompatibility complex. Proc.Natl.Acad.Sci. USA 88, 5197–5201). To knockout the function of H2-M in the mouse, the H2-Ma gene may be the better target for disruption since it exists as a single gene. The H2-M modified transgenic mice that we have generated provide a model in which the H2-Ma gene was disrupted by homologous recombination (HR). The process of generating the knockout mice can be divided into 4 basic stages:

1. Cloning of the H2-Ma gene and preparation of DNA construct for transfection of embryonic stem (ES) cells;
2. Isolating transfected ES cells in which the H2-Ma gene has been knocked out by HR;
3. Generating chimeric mice from mouse embryos injected with the knockout ES cells; and
4. Breeding chimeric mice to obtain knockout mice through germ line transmission.

The present invention utilizes a mouse H2-Ma gene clone to generate transgenic animals in which the H2-Ma gene has been altered. The alterations to the naturally occurring gene can be modifications, deletions and substitutions. Modifications and deletions render the naturally occurring gene nonfunctional, producing a "knockout" animal Substitution of the naturally occurring gene for a gene from a second species results in an animal which produces the gene product of the second species. Substitution of the naturally occurring gene for a gene having a mutation results in an animal which produces the mutated gene product. These transgenic animals are critical for drug antagonist or agonist studies, the creation of animal models of human diseases, and for eventual treatment of disorders or diseases associated with human HLA-DM-mediated immune responses. A transgenic animal carrying a "knockout" of the H2-Ma gene is useful for the establishment of a nonhuman model for diseases involving H2-M equivalents such as HLA-DM in the human.

The sequence of the mouseH2-Ma gene is known (Peleraux et al., 1996, Genomic organization of a mouse MHC class II region including the H2-M and 1mp2 loci. Immunogenetics, 43 204–214). The H2-Ma genomic DNA is cloned from a mouse genomic library and has the expected characteristics of DNA encoding the H2-Ma protein. A transgenic mouse carrying the disrupted H2-Ma gene is generated by homologous recombination of a target DNA construct with the endogenous gene on the chromosome. The transgenic mouse carrying the disrupted H2-Ma gene does not express functional H2-M molecules, and is useful in establishing an in vivo model of human HLA-DM-mediated diseases.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at a subcellular level, such as by targeted recombination or microinjection or infection with recombinant virus. The term "transgenic animal" is not intended to encompass classical cross-breeding or in vitro fertilization, but rather is meant to encompass animals in which one or more cells are altered by, or receive, a recombinant DNA molecule. This recombinant DNA molecule may be specifically targeted to a defined genetic locus, may be randomly integrated within a chromosome, or it may be extrachromosomally replicating DNA. The term "germ line transgenic animal" refers to a transgenic animal in which the genetic alteration or genetic information was introduced into germ line cells, thereby conferring the ability to transfer the genetic information to offspring. If such offspring in fact possess some or all of that alteration or genetic information, they are transgenic animals as well.

The alteration or genetic information may be foreign to the species of animal to which the recipient belongs, or foreign only to the particular individual recipient, or may be genetic information already possessed by the recipient. In the last case, the altered or introduced gene may be expressed differently than the native gene, or not expressed at all.

The altered H2-Ma gene generally should not fully encode the same H2-Ma as native to the host animal, and its expression product should be altered to a minor or great degree, or absent altogether. However, it is conceivable that a more modestly modified H2-Ma will fall within the scope of the present invention.

The genes used for altering a target gene may be obtained by a wide variety of techniques that include, but are not limited to, isolation from genomic sources, preparation of cDNAs from isolated mRNA templates, direct synthesis, or a combination thereof.

A type of target cells for transgene introduction is the ES cells. ES cells may be obtained from pre-implantation embryos cultured in vitro and fused with embryos (M. J. Evans et al., Nature 292: 154–156 (1981); M. O. Bradley et al., Nature 309: 255–258 (1984); Gossler et al. Proc. Natl. Acad. Sci. USA 83: 9065–9069 (1986); Robertson et al., Nature 322, 445–448 (1986); S. A. Wood et al. Proc. Natl. Acad. Sci. USA 90: 4582–4584 (1993)). Transgenes can be efficiently introduced into the ES cells by standard techniques such as DNA transfection or by retrovirus-mediated transduction. The resultant transformed ES cells can thereafter be combined with blastocysts from a non-human animal The introduced ES cells thereafter colonize the embryo and contribute to the germ line of the resulting chimeric animal (R. Jaenisch, Science 240: 1468–1474 (1988)).

Since H2-M is an independent component of a complex mechanism, the proteins, including that encoded by the H2-Ma DNA, must be examined both individually and as a group if their contribution to the mechanisms of immune responses are to be understood. One approach to the problem of determining the contributions of individual genes and their expression products is to use isolated genes to selectively inactivate the native wild-type gene in totipotent ES cells (such as those described herein) and then generate transgenic mice. The use of gene-targeted ES cells in the generation of gene-targeted transgenic mice was described 1987 (Thomas et al., Cell 51:503–512, (1987)) and is reviewed elsewhere (Frohman et al., Cell 56:145–147 (1989); Capecchi, Trends in Genet. 5:70–76 (1989); Baribault e al., Mol. Biol. Med. 6:481–492, (1989); Wagner, EMBO J. 9: 3025–3032 (1990); Bradley et al., Bio/Technology 10: 534–539 (1992)).

Techniques are available to inactivate or alter any genetic region to any mutation desired by using targeted homologous recombination to insert specific changes into chromosomal alleles. However, homologous plasmid-chromosome recombination was detected only at frequencies between $10^{-6}$ and $10^{-3}$ in mammalian cells (Lin et al., Proc. Natl. Acad. Sci. USA 82:1391–1395 (1985); Smithies et al., Nature 317: 230–234 (1985); Thomas et al., Cell 44:419–428, (1986); Song et al., Proc. Natl. Acad. Sci. USA 84:6820–6824 (1987)). Nonhomologous plasmid-chromosome interactions are more frequent, occurring at levels 105-fold (Lin et al., Proc. Natl. Acad. Sci. USA 82:1391–1395 (1985)) to $10^2$-fold (Thomas et al., Cell 44:419–428 (1986); Song et al., Proc. Natl. Acad. Sci. USA 84:6820–6824 (1987)) greater than comparable homologous insertion.

To overcome this low frequency of homologous recombination in murine ES cells, various strategies have been developed to detect or select rare homologous recombinants. One approach for detecting homologous alteration events uses the polymerase chain reaction (PCR) to screen pools of transformant cells for homologous insertion, followed by screening individual clones (Kim et al., Nucleic Acids Res. 16:8887–8903 (1988); Kim et al., Gene 103:227–233 (1991)). Alternatively, a positive genetic selection approach has been developed in which a marker gene is constructed which will only be active if homologous insertion occurs, allowing these recombinants to be selected directly (Sedivy et al., Proc. Natl. Acad. Sci. USA 86:227–231 (1989)). One of the most powerful approaches developed for selecting homologous recombinants is the positive-negative selection (PNS) method developed for genes (such as H2-Ma) for which no direct selection of the alteration exists (Mansour et 4., Nature 336:348–352: (1988); Capecchi, Science 244:1288–1292, (1989); Capecchi, Trends in Genet. 5:70–76 (1989)). The PNS method is more efficient for targeting genes which are not expressed at high levels because the marker gene has its own promoter. Nonhomologous recombinants are selected against by using the Herpes Simplex virus thymidine kinase (HSV-TK) gene and selecting against its nonhomologous insertion with the herpes drugs such as gancyclovir (GANC) or FIAU (1-(2-deoxy 2-fluoro-B-D-arabinofluranosyl)-5-iodouracil). By this counter-selection, the number of homologous recombinants in the surviving transformants can be increased.

As used herein, a "targeted gene" or "Knockout" (KO) is a DNA sequence introduced into the germline of a non-human animal by way of human intervention, including but not limited to, the methods described herein. The targeted genes of the invention include DNA sequences which are designed to specifically alter cognate endogenouos alleles.

MHC class II molecules bind peptides derived from exogenous proteins and present these peptides at the cell surface where they can be recognized by T cells. Two ways can be envisioned to modify the presenting function of MHC class II molecules. Either the expression of the MHC class II molecules themselves can be blocked, or the process of peptide loading onto newly synthesized MHC class II molecules can be blocked. Mice lacking MHC class II molecules have been generated (Cosgrove et al., 1991, Mice lacking MHC class II molecules. Cell 66, 1051–66). They have decreased finction of the immune system with only low numbers of MHC class 11-reactive T cells, and while the numbers of B cells are normal their ability to produce certain antibodies is affected. Their ability to resist viral infection appears to be normal (Bodmer et al., 1993, Environmental modulation of the autonomy of cytotoxic T lymphocytes. Eur. J. Immunol. 23, 1649–54; Laufer et al., 1993, Autoimmune diabetes can be induced in transgenic major histocompatibility complex class II-deficient mice. J. Exp. Med. 178, 589–96). Regulation of MHC class II expression is so complex that it is not totally clear which transcription factors should be targeted by a potential drug. Control of peptide loading is potentially easier to achieve since recent data demonstrate that HLA-DM acts as an enzyme catalyzing the exchange of low affinity peptides for high affinity peptides on MHC class II molecules. However, not all antigens are equally affected by the absence of HLA-DM and it is likely that the absence of HLA-DM will have a less pronounced effect than the total absence of MHC II molecules. The expression level of HLA-DM is at least ten-fold less than the MHC class II molecules and the invariant chain. The relatively small quantity of HLA-DM relative to other MHC class II elements is consistent with its catalytic finction. Unlike MHC class II or the invariant chain, HLA-DM is located mainly in the endosomal compartment which is easily accessible by small molecule drugs. The small quantity and the intracellular location of H2-M makes it an attractive drug target. It appears likely that a drug which could block the function of HLA-DM would be a useful therapeutic agent, and thus H2-M knockout mice will be useful to demonstrate the in vivo function of H2-M and the effects on MHC class II function. Based on the cellular data it can be expected that many (but not all) antigens are poorly presented by MHC class 11 molecules in the H2-M knockout mice (Brooks et al., 1994, Antigen presentation and assembly by mouse I-Ak class 11 molecules in human APC containing deleted or mutated HLA DM genes. J. Immunol. 153, 5382–92; Mellins et al., 1990, Defective processing and presentation of exogenous antigens in mutants with normal HLA class II genes. Nature 343, 71–4). The decreased antigen presentation will most likely lead to increased susceptibility to infections and the extent of this effect can be studied in the H2-M knockout mice.

H2-M knockout mice will help to define the role of MHC class II and peptides for thymic development of T cells. Development of MHC class II-restricted T cells requires expression of MHC class II molecules in the thymus. It is not clear however, how the developing T cells recognize MHC class II molecules and whether the MHC class II molecules in the thymus are loaded with peptides. In the H2-M knockout mice, the levels of MHC class II at the cell surface are normal but most of the MHC class II molecules are loaded with invariant chain peptides. H2-M knockout mice develop lower than normal numbers of MHC class II-restricted T cells, suggesting that the development of these cells require diversity of the peptides associated with MHC II in the thymus. Since the development of T cells is shown to require the presence of H2-M, drugs that block the expression or the function of HLA-DM in human cells may have the side-effect of compromising the T cell repertoire in young individuals. To further analyze the thymocyte selection procedure in H2-M knockout mice, these mice are bred with T cell receptor transgenic mice. The T cell receptors of these mice all have the same specificity, thus enabling the study of the effect of H2-M on the development of specific T cell receptors with known reactivity.

The effect of H2-M on the progression of chronic inflammatory disease and graft rejection is also studied in H2-M knockout mice. The possible low level and poor antigen presentation of MIC class II molecules in the absence of H2-M predicts that the activation and effector function of MHC class II-restricted T cells will be affected. Drugs targeting the function of HLA-DM may have the therapeutic effect of slowing down the progression of autoimmune diseases and in the prevention of graft rejection. The effects of the absence of MHC class II molecules have been analyzed in several mouse models of autoininune diseases and showed that in most cases the severity of the disease is decreased (Reviewed in Grusby and Glimcher, 1995, Immune responses in MHC class II-deficient mice. Annu. Rev. Immunol. 13, 41714 35). The H2-M knockout mice that are disclosed herein are crossed with the different autoimmune disease mouse models to study the effect of H2-M in the progression of autoimmune diseases. Similarly, the involvement of H2-M in transplantation is studied in the H2-M knockout mice.

Cells from H2-M knockout mice are used to present specific antigenic peptides. Antigen presenting cells derived from normal mice, have MHC class II molecules with stably bound peptides. MHC class II molecules on normal cells can be loaded with exogenous peptides, but only a minor part of the MHC class II molecules bind the added peptide. In contrast the antigen presenting cells from mice lacking H2-M have MHC class II molecules containing invariant chain peptides to a large extent. These peptides can be exchanged for exogenously added peptides by lowering the pH and by adding recombinant H2-M to the outside of the cells. This effect is utilized in a situation where antigen presenting cells are collected from the H2-M knockout mice and loaded with peptides of choice in vitro. Cells thus loaded with antigenic peptides are then used as antigen presenting cells efficiently presenting the added peptide either for stimulation of T cells in vitro or for injection into animals for in vivo stimulation. Likewise, a HLA-DM blocking drug is used in a similar manner for treatment of diseases where the reactivity of the immune system against a particular antigen is insufficient, e.g. in cancer patients. In this case antigen presenting cells are collected from the patient and treated with the drug blocking HLA-DM while the cells are kept in culture long enough to allow peptide-containing MHC class II molecules to be replaced at the cell surface by invariant chain peptide-containing MHC class II molecules. These cells can then be efficiently loaded with tumor-derived peptides as described above and then administered back into the patient, thus providing efficient antigen presentation to the patients own T cells. Antigen specific T cell tolerance can be induced by presenting T cells to antigen presenting cells loaded with a high dose of a specific antigenic peptide. Induction of T cell tolerance is an ideal situation clinically, because it means that a long term drug treatment is unnecessary. In the case of autoimmune diseases in which the antigen specificity of the reacting T cells are known, efficent loading of antigen presenting cells with a particular antigenic peptide is used to induce T cell tolerance.

The following Examples are presented for the purpose of illustrating the present invention and are not to be construed as a limitation on the scope of this invention.

EXAMPLE 1

Isolation of the Mouse H2-Ma Genomic Clones

To disrupt a specific gene by homologous recombination, DNA constructs containing the disrupted gene is needed for transfection of ES cells. First of all, the mouse H2-Ma gene is needed for making the DNA construct. The mouse H2-Ma gene was known to be located at the 5' proximal region of the H2-Mb2 gene (Cho et al., 1991, A cluster of transcribed sequences between the Pb and Ob genes of the murine major histocompatibility complex, Proc.Natl.Acad.Sci.USA 88, 5197–5201). To clone the mouse genomic DNA containing the H2-Ma gene, a mouseH2-Mb2 cDNA (Peleraux et al., 1995, Genomic organization of a mouse MHC class II region including the H2-M and lmp2 loci., Immunogenetics, in press) was labelled with 32-P radioisotope and used as a probe to screen $4 \times 10^5$ phage plaques prepared from a 129 SV mouse genomic library. Seven phage clones hybridized to the probe and were isolated for characterization. Two clones were found to contain the complete H2-Ma gene and one of them (clone 2) was chosen for further analyses. FIG. 1 shows the region of the H2-Ma gene covered by clone 2. The restriction map of the H2-Ma gene was obtained from the analysis of clone 2.

EXAMPLE 2

Preparation of Gene-Targeting Constructs

The DNA construct was made in a pUC plasmid vector. A 6.7 Kb genomic fragment which covers the majority of the H2-Ma gene except exon 1 and part of intron 1, was obtained from the clone 2 and used in the construct as a homologous region for recombination (FIG. 1). The neo cassette containing the neomycin resistant gene was placed into the second exon of the H2-Ma gene. Two types of constructs were made in which the neo cassette was either in the same or the opposite orientation of the H2-Ma gene. A deletion of 61 bp in exon 2 was also made at the site where the neo cassette was placed. The Herpes simplex virus type-1 thymidine kinase (HSV tk) gene was placed at the 3' end of the homologous region.

EXAMPLE 3

Isolation of Gene-Targeted ES Cell Lines

Transfection of ES Cells

The DNA construct was linearized by complete digestion with NotI, SfiI or a combination of the two restriction enzymes. DNA was then precipitated by 2 volumes of ice cold ethanol at −20° C. for 1 hour. Precipitated DNA was collected by centrifugation, rinsed once with 0.5 ml 70% ethanol, air dried and then dissolved at 1 mg/ml in phosphate buffered saline (Gibco).

ES cells E14 (Hooper et al., 1987, HPRT-deficient (Lesch-Nyhan) mouse embryos derived from germline colonization by cultured cells. Nature 326, 292–295) were maintained at an undifferentiated stage by co-culturing with embryonic fibroblasts (EF) and in culture medium (15% FCS, 1 mM sodium pyruvate, 0.1 mM b-mercaptoethanol, 2 mM L-glutamine, 100 U penicillin and 100 U streptomycin) containing 1000 U/ml leukemia inhibitory factor (LIF) (Gibco). EF cells were primary fibroblast cultures prepared from day 15–17 mouse fetuses according to the method described by Robertson (Robertson, 1987, Embryo-derived stem cell lines. Chaptor 4. from "Teratocarcinomas and embryonic stem cells. A practical approach" Editor: Robertson, E. J. IRL Press, Oxford—Washington D.C.). EF were treated with 10 ug/ml mitomycin C (Sigma) in culture medium for 2 hours to stop cell division prior to their use as feeder cells. For DNA transfection, ES cells were harvested by trypsin treatment and resuspended at $6.25 \times 10^6$ cell/ml in culture medium. DNA construct of 20 ug was added into 0.8 ml of ES cell suspension for electroporation at 250 uF and 340 Volts using the Gene Pulser (BioRad).

Transfected ES cells were plated onto EF-coated 90 mm plates at $2.5 \times 10^6$/90 mm plate in culture medium. Two days later, cells were subject to drug selection in medium containing 400 ug/ml G418 (Geneticin, Gibco) and 2 uM GANC (Cytosin, Syntex). Culture medium was changed daily. Massive cell death was obvious starting at about day 4 and most of the dead cells were removed through the daily medium change by about day 8. Surviving cell colonies were observable under microscope by about day 7.

PCR Screen for Homologous Recombination in ES Cells

The size of ES colonies on day 11 after transfection was large enough for PCR screening. To collect cell colonies, culture medium in the 90 mm plates was aspirated and 10 ml PBS was added. Individual cell colonies were located with the aid of a stereomicroscope, collected in a 20 ul volume and transferred into 96-well plates. To prepare single cell suspension of the ES colonies, 25 ul of 0.25% trypsin (Gibco) was added per well in 96 well-plates. After 8 minutes of trypsin treatment at 37° C., 25 ul of culture medium was added. All the ES colonies were still maintained in culture as master plates while they were screened by PCR for homologous recombination events. To prepare master plates, 60 ul of each cell sample was transferred to 96 well-plates which had been coated with EF cells and contained 180 ul/well of the culture medium containing G418 and GANC.

For the first round PCR screen, each cell lysate sample was prepared from 12 cell colonies which arrayed as one row of samples in the 96 well-plates. After the preparation of master plates, the remaining cell samples of about 90 uliwell on every row of the plates were pooled and cells were pelleted. After draining all the medium, cells were lysed by adding 30 ul distilled water and brief vortexing. Cell lysates were prepared by first heating at 95° C. for 10 minutes, followed by an addition of 1 ul proteinase K (10 mg/ml in water) with brief vortexing, a 90 minute incubation at 50° C. for proteinase K digestion, and then 10 minutes at 95° C. for heat inactivation of proteinase K.

PCR was carried out using the 9600 GeneAmp system (Perkin Elmer). The reaction mixtures contained 5 ul cell lysate, 4 uM of each of the two oligonucleotide primers, 200 uM each of DATP, dTTP, dCTP, and dGTP, and 5 U AmpliTaq DNA polymerase in PCR buffer (10 mM Tris-Cl, pH8.3, 50 mM KCl and 1.5 mM MgCl2). The reaction condition was 3 cycles of 2' at 94° C., 2' at 60° C., and 2' at 72° C., then 40 cycles of 15" at 94° C., 15" at 60° C., and 1' at 72° C., followed by 7' at 72° C. For DNA construct in which the neo gene and the H2-Ma gene are of the same orientation, PCR primers that were used to amplify homologous recombination were: MA3S (5'-GGATTCCTGTCAGGAGTTTCAAAG-3') [SEQ.ID.NO.:1], Neo-134R (5'-AAGCGCATGCTCCAGACTGCCTT-3') [SEQ.ID.NO.:2], and the size of the amplified DNA is expected to be about 1 Kb.

For DNA construct in which the neo gene and the H2-Ma gene are of opposite orientation, PCR primers were: MA3S and neo-1858 (5'-GCCAAGTFCTAATTCCATCAG-3') [SEQ.ID.NO.:3], and the size of the amplified DNA is expected to be about 0.98 Kb.

To detect the specific DNA fragment amplified by PCR, 20 ul of the PCR samples were separated according to size by 1% agarose gel electrophoresis, blotted onto nylon membranes (Hybond, Amersham), and hybridized to the $P^{32}$-labelled oligonucleotide probe A (5'-CCAGTTCTGTCAGCACAAGGTCTGGAGTGTTTAGGT-3') [SEQ.ID.NO.:4]. PCR samples with the expected size of DNA bands detected by the oligo probe were considered as putative positive groups for further screening.

ES cells in master plates after about 3–4 days culture were ready for spliting. Cell colonies in the positive groups were screened individually by a second round of PCR to identify the positive colonies. To maintain the positive groups in culture, cells in the wells were trypsinized by first removing the culture medium, rinsing once with 50 ul PBS, treating with 40 ul 0.25% trypsin for 5 minutes at 37° C., followed by adding 90 ul culture medium. Cells were then resuspended and 20 ul of them were transferred to master plates which had been coated with EF and filled with 200 ul culture medium containing G418 and GANC. The remaining cells (110 ul/well) were collected individually into eppendorf tubes. Cell lysates were prepared and homologous recombination signals were amplified by PCR and detected by hybridization using the oligonucleotide probes mentioned above.

Confirmation of Gene-Targeted ES Cells by Genomic Southern Hybridization

ES cells derived from the positive colonies in PCR screening were expanded in culture and DNA was purified from the cells. Genomic DNA was digested with ApaI, resolved on a 1% agarose gel, blotted onto Hybond-N+ membrane (Amersham), and hybridized to a $^{32}$P-labeled DNA fragment as shown in FIG. 1. The probe was a 0.6 Kb EcoRI/BamHI fragment (the EcoRI site was derived from the lambda vector and the vector sequence constituted less than 8bp in the whole probe) that hybridized to a 2.8 Kb ApaI fragment in the normal H2-Ma gene and to a 1.8 Kb ApaI fragment in the H2-Ma gene that had undergone homologous recombination with the targeting construct. The disruption of the H2-Ma gene by homologous recombination is shown in FIG. 1. The restriction map of the wild-type H2-Ma gene (A - ApaI, H - HindIII, N - NotI, S-StuI, Sf-SfiI) with the numeric filled boxes being exons is shown. The gene targeting construct of the H2-Ma gene is shown with the neomycin cassette (neo) placed in the second exon of the H2-Ma gene and a 61 base pair deletion was also created in exon 2 where neo was placed. The Herpes Simplex Virus type 1 thymidine kinase (HSV-TK) gene was placed at the 3' end of the construct. The structure of the disrupted H2-Ma gene after homologous recombination between the targeting construct and the endogenous H2-Ma gene is also shown.

EXAMPLE 4

Injection of the Gene-Targeted ES Clone into Donor Blastocysts

The gene-targeted ES cell line with the disrupted H2-Ma gene was characterized by PCR and confirmed by Southern hybridization analysis. ES cells were then separated from their feeder cells by treating the cell culture with trypsin, allowing the feeder cell to attach for 30–45 min, and removing the unattached ES cells. The ES cells were injected into C57BL/6J recipient blastocysts using techniques described previously (Bradley, A. "Production and analysis of chimeric mice. In Teratocarcinomas and Embryonic Stem Cells: A Practical Approach", E. J. Robertson, ed.Oxford:IRL Press, (1987), pp113–151).

Mouse embryos at about 3.5 day gestation stage were collected from the uteri of superovulated C57BL/6J mice. About 10–15 ES cells were injected into the blastocoel cavity of the embryos. Injected embryos were transferred into the uteri of about 2.5 day pseudopregnant CD1 mice, and mice developed from these embryos were born 17 days later. A total of 16 chimeric mice were obtained from embryo injection with the H2-Ma knockout cell lines. Since ES cells E14 that we used were derived from the 129 Ola mouse strain which is homozygous for the dominant agouti (A) coat color genes, As the ES cell line E14 is homozygous for the agouti (A) coat color gene, penetrance of ES cells into the injected (black coat color) C57BL/6 blastocysts give rise to chimeric coat color mice.

EXAMPLE 5

Breeding Chimeric Mice

The chimeric male mice are bred to wild-type C57BL/6 (black coated) female mice. Some of the progeny from the chimera X C57BL/6 cross are expected to be agouti if the chimeric male had ES cell genetic material incorporated into its germ line (agouti is dominant to black coat color). These crosses are performed to test for the transfer of ES cell genetic information, including the disrupted H2-Ma gene, to its offspring.

To determine the H2-Ma genotypes, genomic DNA was purified from about 1 cm of tail from each mouse after weaning. The genomic DNA was isolated as described (Laird et al., supra), followed by phenol and phenol:chloroform extractions and ethanol precipitation. Southern hybridization analysis (as described herein) was used to identify offspring which contained the disrupted H2-Ma gene. These transgenic offspring are heterozygous for the H2-Ma gene disruption. Both transgenic heterozygous and nontransgenic mouse (tail) genomic DNAs were digested with ApaI, resolved on a 1% agarose gel, blotted onto Hybond-N+ membrane, and hybridized with 3' flanking DNA probes to confirm the transgenic H2-Ma gene structure. Southern hybridization analysis confirmed that the structure of the altered H2-Ma gene was identical to that predicted, and previously characterized in the H2-Ma-targeted ES clones. FIG. 2 shows the analysis of mouse tail DNA by Southern blot, with hybridization profiles of wild-type (+/+), heterozygous (+/–), and homozygous (–/–) mice shown.

EXAMPLE 6

Figure 1B:
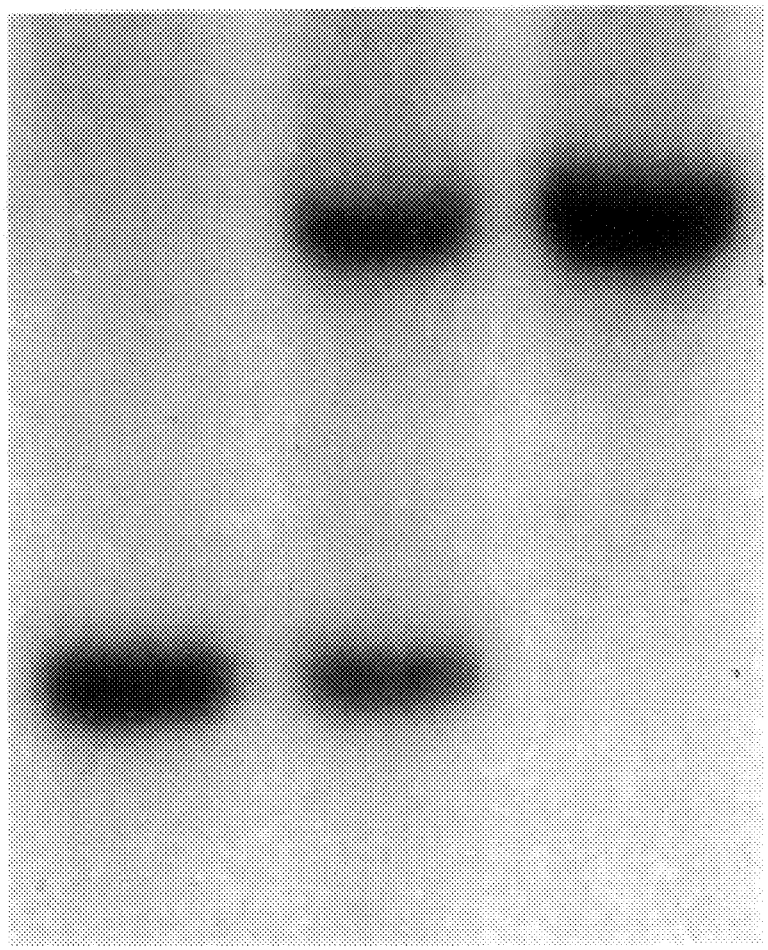

Breeding Heterozygous Mice and Generation of Homozygous H2-Ma Deficient Mice Male and female transgenic mice, each of which contained one copy of the altered H2-Ma gene (heterozygous mice), were mated with each other to generate mice in which both copies of the H2-Ma gene are the targeted, altered transgenic H2-Ma gene. It was predicted that one fourth of the mouse embryos would be homozygous for the altered H2-Ma gene. Surviving offspring are genotyped by Southern hybridization as described above. Homozygous mutant mice are born at a ratio of 1 in 4 pups if the defective gene does not affect embryo development. Homozygous mutant mice are identified by analysis of tail DNA samples, in which only the 1.8 kb ApaI cut DNA band derived from the disrupted gene, but not the 2.8 kb DNA band from the intact H2-Ma gene is hybridized to the 0.6 kb flanking probe (FIG. 1B). It is determined that 33% (15 mice) of a total of 45 offspring mice were homozygous (−/−) for the disrupted H2-Ma gene, 35.5 % (16 mice) were heterozygous and 31.1% (14 mice) were wild-type (+/+) for the H2-Ma gene.

EXAMPLE 7

Characterization of Homozygous H2-Ma Deficient Mice

Figure 1C:
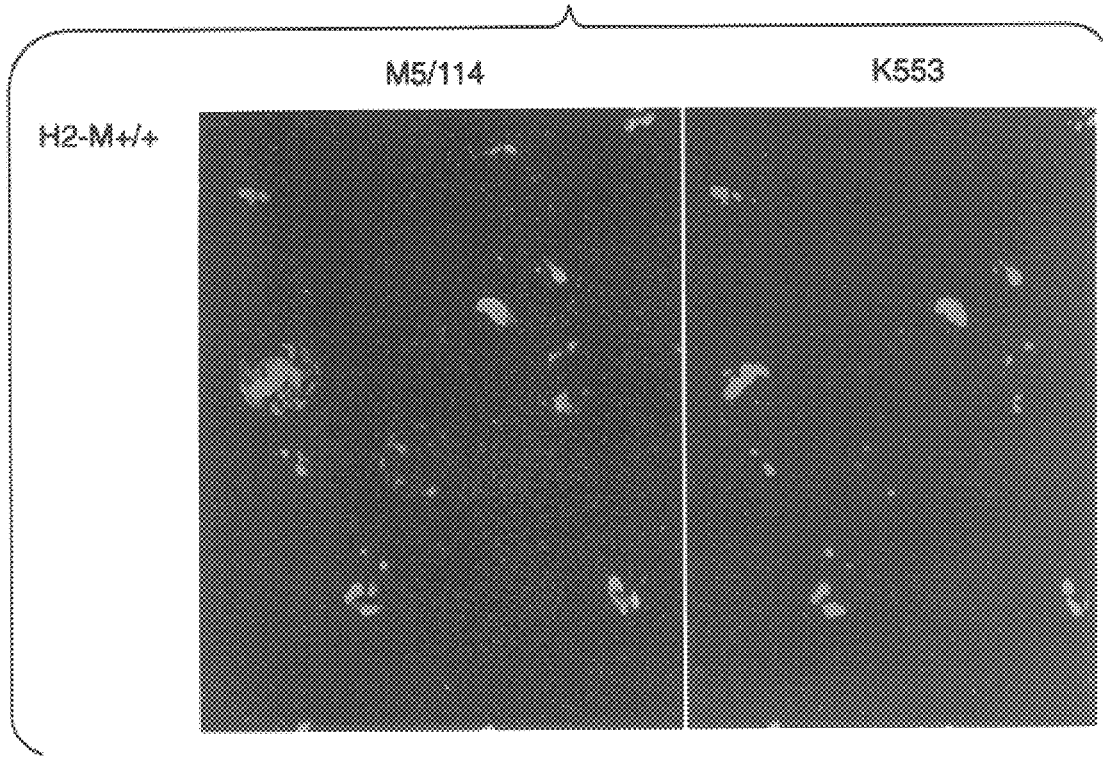
Figure 1D:
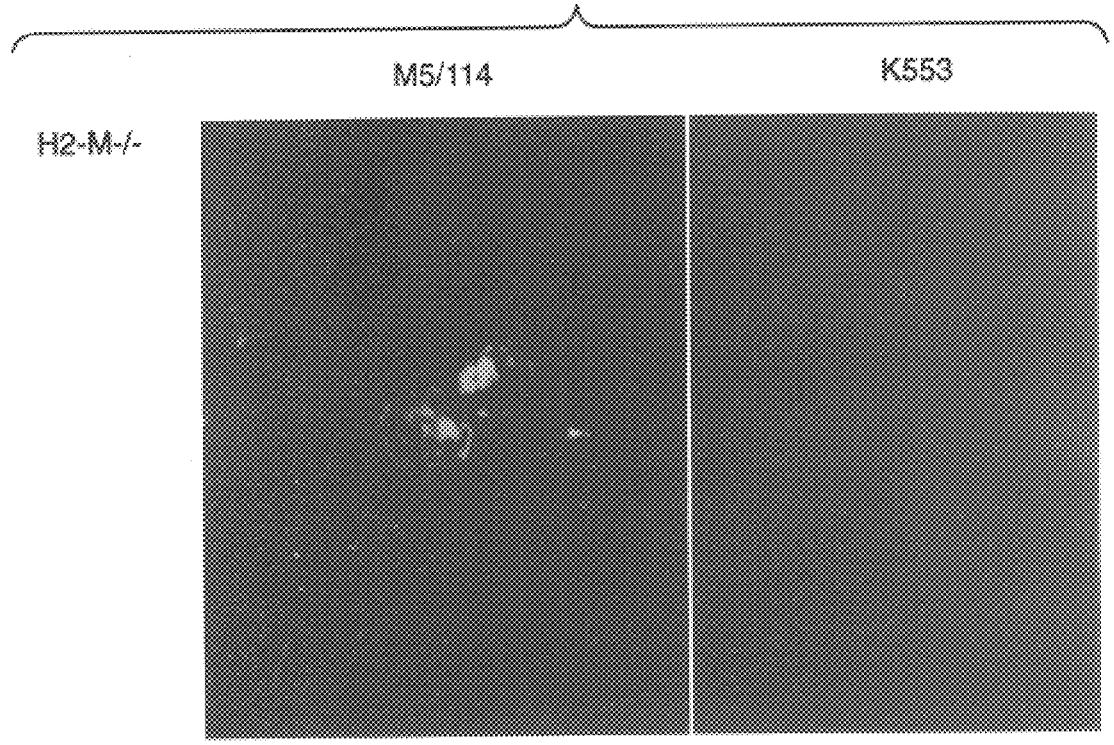
Figure 1E:
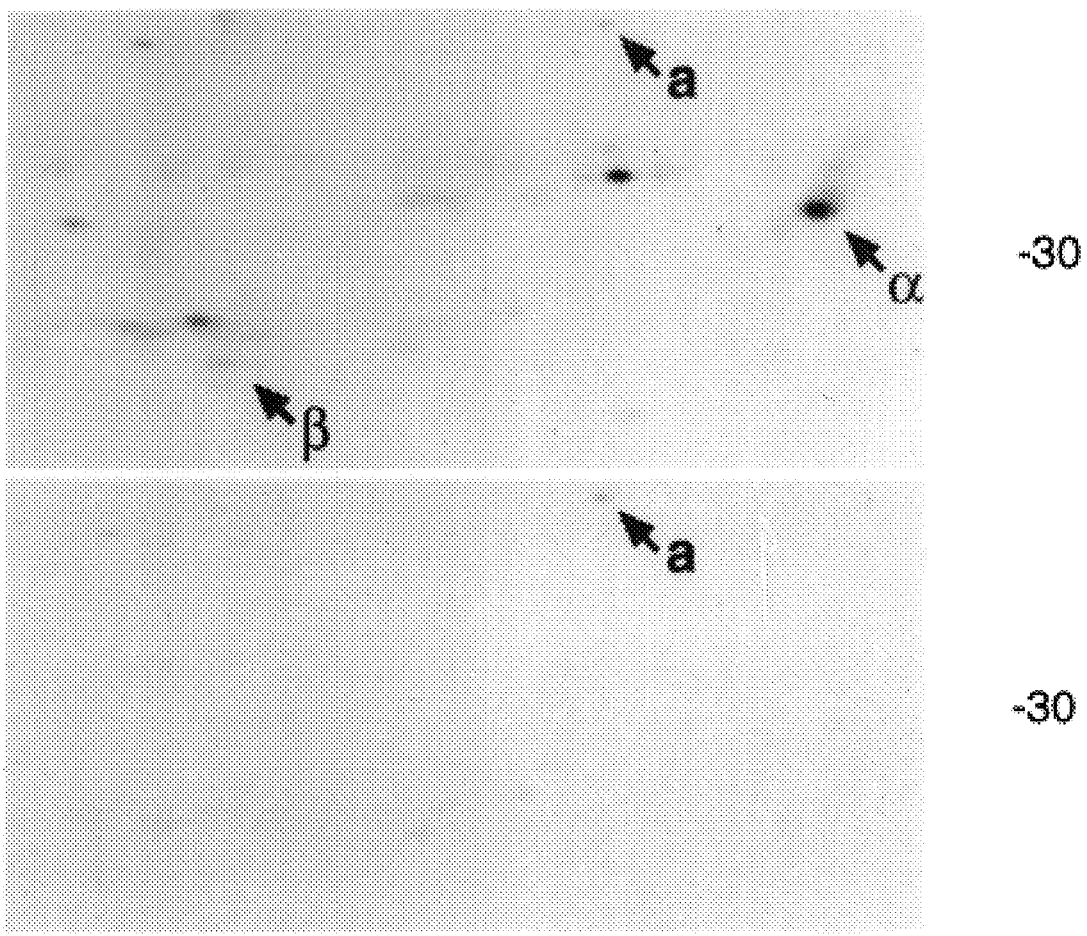

Splenocytes from H2-M+/+ (wild-type) and H2-M−/− (deficient) mice were analyzed for H2-M expression using indirect immunofluorescence. Spleen cells were cultured on cover slips coated with Cell-Tak (Collaborative Biomedical Research) before fixation with 4% formaldehyde-PBS. After fixation, cells were washed with 50 mM $NH_4Cl$ and PBS. Antibody incubations were made in PBS with 0.6% fish skin gelatin and 0.2% saponin for permeabilization. Texas-Red-labeled rabbit antibody to immunoglobulin G (IgG) (Molecular Probes) and fluorescein isothiocyanate (FlIC)-labeled rat antibody to IgG (Cappel) were used as secondary reagents. Fluorescent cells were imaged with the use of a Bio-Rad confocal microscope. In H2-M+/+ mice, H2-M staining was located in vesicular structures (FIG. 1C, red), while no H2-M staining was detected in cells from H2-M−/− mice (FIG. 1D, red). Costaining with anti-H2-$A^b$ monoclonal antibody (mAb) MS5/ 14 showed no distinct staining differences between the two cell types (Compare FIG. 1C and 1D, green). The absence of normal H2-M protein in the mutant mice was confirmed by two-dimensional gel electrophoresis of immunoprecipitated H2-M from metabolically labeled splenocytes. While precipitates from wild-type cells contained both H2-Ma and H2-Mb, no H2-M protein was detected in the precipitate from the H2-M−/− cells (FIG. 1E).

Figure 2A:
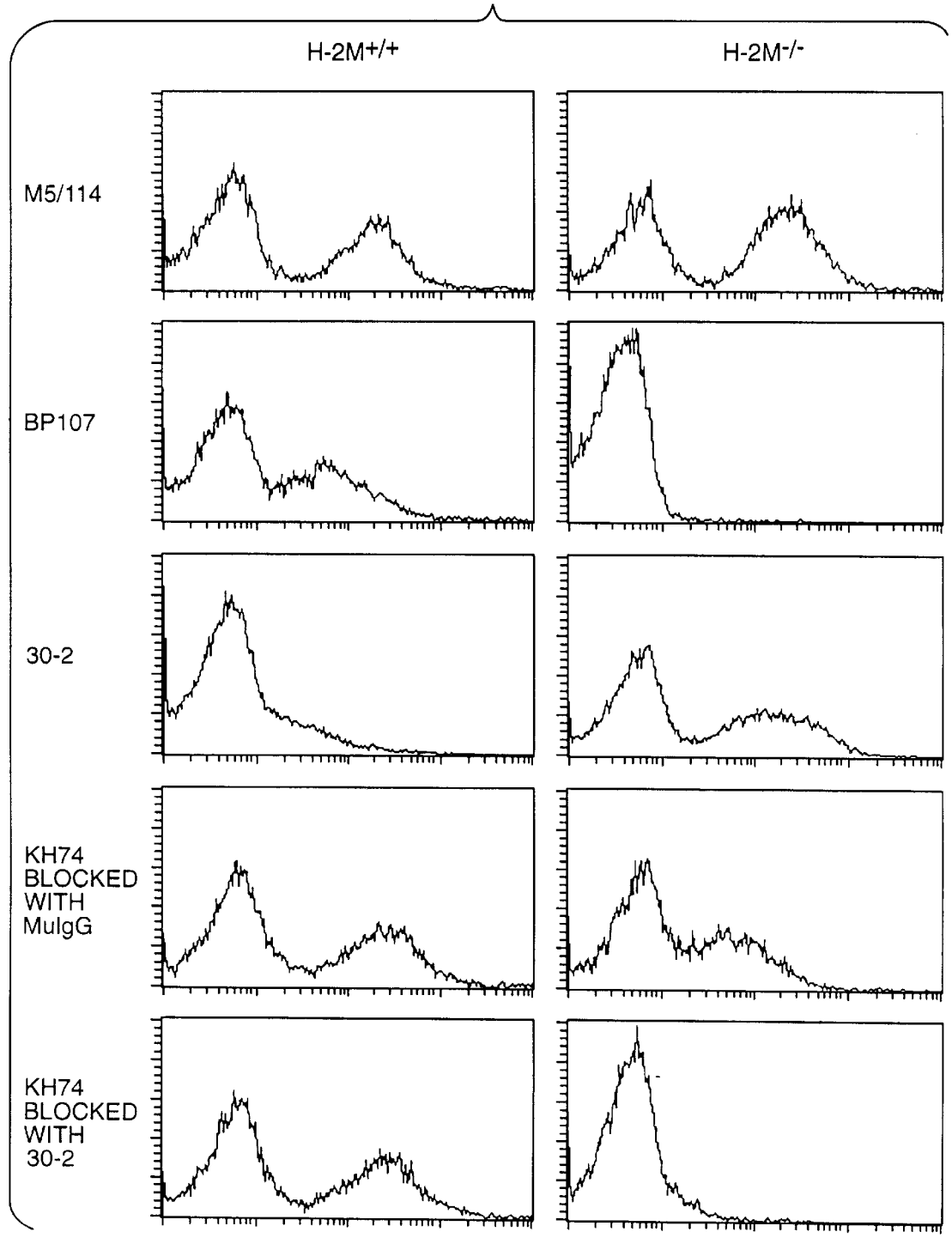
FIG. 2 Panels A, B, C, and D. Expression of H2-A in lymphoid tissues of H2-M−/− and H2-M+/+ littermates. (A) Lymph nodes cells were stained with antibodies reactive with either H2-A$^b$ (M5/114, BP107, KH74) or an antibody to CLIP-loaded H2-A$^b$ (30-2) and analyzed by flow cytometry. Binding of KH74 to H2-M−/− cells was blocked by prior incubation with 30-2 but not with irrelevant mouse IgG (MuIgG). (B) Thymus sections were stained with either K553, reactive with H2-M, with anti-H2-A$^b$ reactive mAbs (M5/114, BP107), or with anti-CLIP mAb (30-2). (C and D) H2-M+/+ and H2-M−/− splenocytes were labeled for 30 min and analyzed immediately (0) or after various periods of incubation with unlabeled medium (hours) as indicated. H2-A$^b$ molecules were immunoprecipitated with M5/114. Immunoprecipitates were harvested with protein G-sepharose, washed, and resuspended in SDS-PAGE sample buffer containing 2% SDS without (FIG. 2C) or with 10 mM dithiothreitol (FIG. 2D). Samples were left at room temperature for 20 minutes (FIG. 2C) or boiled for 5 minutes (FIG. 2D). Samples were separated on 7.5 to 12.5% polyacrylamide gels directly. Abbreviations are as follows: α, H2-A$^b$α; β, H2-A$^b$β; an and αβ*, H2-A$^b$ dimers. Size markers are in kilodaltons; 1ip3 1, invariant chain p31.

To determine the effect of H2-M on the cell surface expression of MHC class II, lymph node cells from wild-type and H2-M deficient mice were incubated with a panel of H2-$A^b$-reactive mAbs and analyzed by flow cytometry (FACS). Several of the mAbs (M5/114, FIG. 2A, Y3P and AF6–120.1) stained wild-type and mutant cells with equal intensity indicating that the cell surface levels of H2-$A^b$ were comparable (FIG. 2A). In contrast to these mAbs, differential staining was observed with two other anti-H2-$A^b$ mAbs: BP107 did not stain mutant cells at all, while KH74 stained mutant cells with reduced intensity (FIG. 2A). These findings suggest that the H2-$A^b$ conformation on the H2-M−/− cells might be different from the wild type control cells. In view of the well documented findings implicating DM in the removal of CLIP from class II molecules (Sloan et al., 1995, Nature 375, 802. Denzin and Cresswell. 1995. Cell 82, 155. Sherman et al., 1995. Immunity 3, 197). The reduced binding of some anti-H2-$A^b$ mAb to H2-M−/− cells, could reflect a failure to exchange CLIP for other peptides. To examine this possibility mutant cells were stained with mAb 30-2 which reacts with CLIP-associated H2-$A^b$ (Morkowski et al., 1995, J.Exp.Med. 182, 1403). In contrast to the weak reactivity with wild type cells, H2-M−/− cells stained strongly with mAb 30-2 (FIG. 2A). Moreover, pre-incubation with mAb 30-2 completely blocked reactivity of anti-H2-$A^b$ mAb KH74 to mutant cells, while the same treatment had no effect on KH74 staining of H-2M+/+ control cells (FIG. 2A). Thus, virtually all class II molecules appeared to contain CLIP.

Figure 2B:
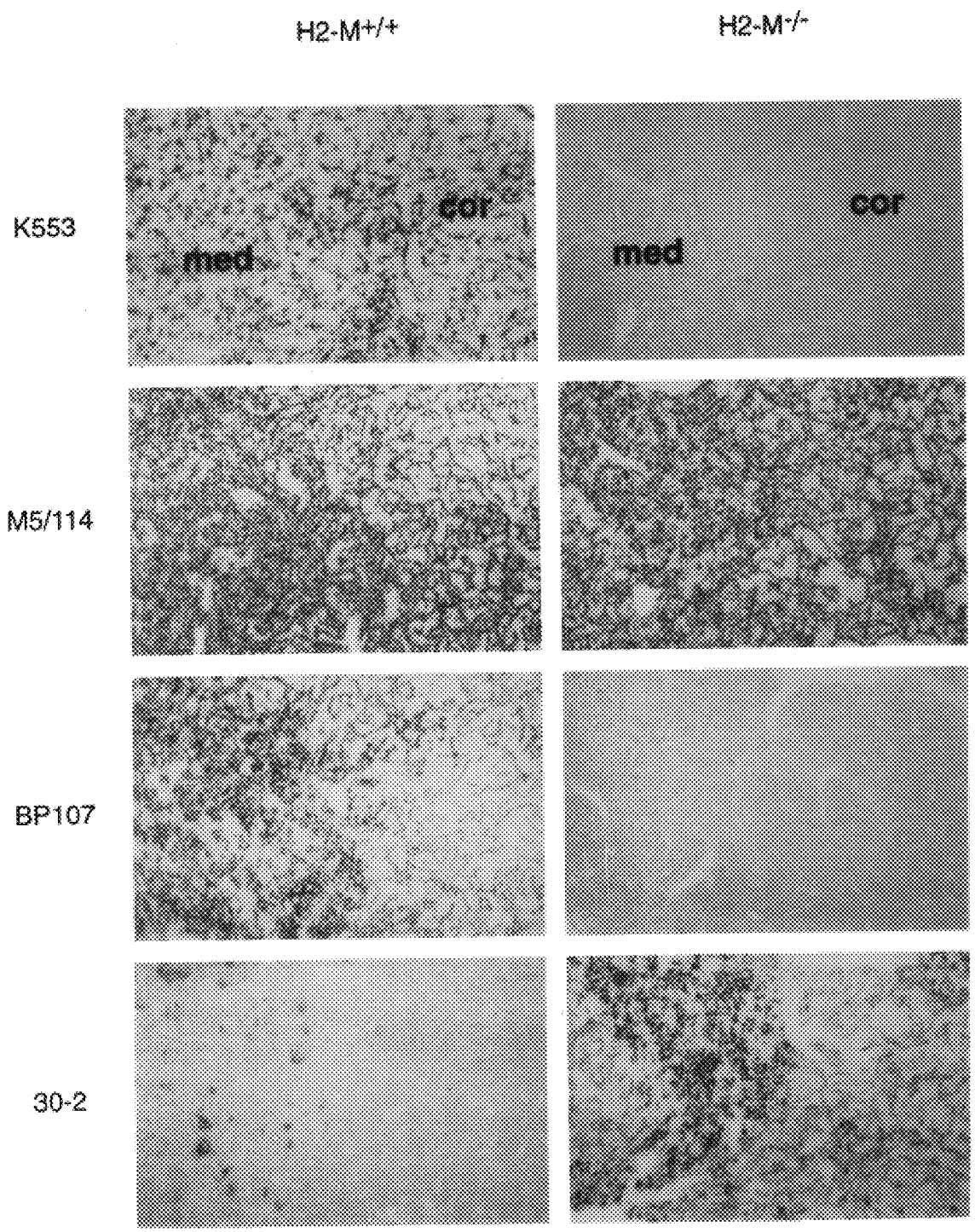

Immunohistochemical analysis of tissue sections from H2-M−/− mice confirmed the FACS analysis findings. Thymus cryostat sections were stained for H2-M with the use of rabbit antiserum K553 followed by biotinylated rabbit antibody to IgG (Jackson ImmunoResearch); for H2-Ab, with the used of biotinylated 30-2 mAbs. Bound antibodies were detected with alkaline phaosphatase-conjugated streptavidin (Jackson ImmunoResearch) followed by colorimetric substrate. Thus, H-2M expression in the lymphoid tissues of mutant mice was undetectable, whereas in wild type mice, H-2M expression was observed in B cells, macrophages and dendritic cells in the spleen and lymph nodes. In normal thymus, H-2M was expressed in cortical epithelial cells and in the medulla, but was completely undetectable in the H2-M−/− thymus (FIG. 2B). Class II expression in the thymus of the mutant mice was comparable to the wild-type control when analyzed by mAb M5/114, while no staining was observed with mAb BP107 in the mutant thymus (FIG. 2B). Similar to the class II molecules in lymph node B cells, the class II molecules in the H2-M−/− thymus appeared to contain mainly CLIP, since both epithelial cells and bone marrow-derived APCs stained strongly with mAb 30-2. In contrast, this antibody stained only few scattered cells in the medulla of the wild-type thymus (FIG. 2B).

Figure 2C:
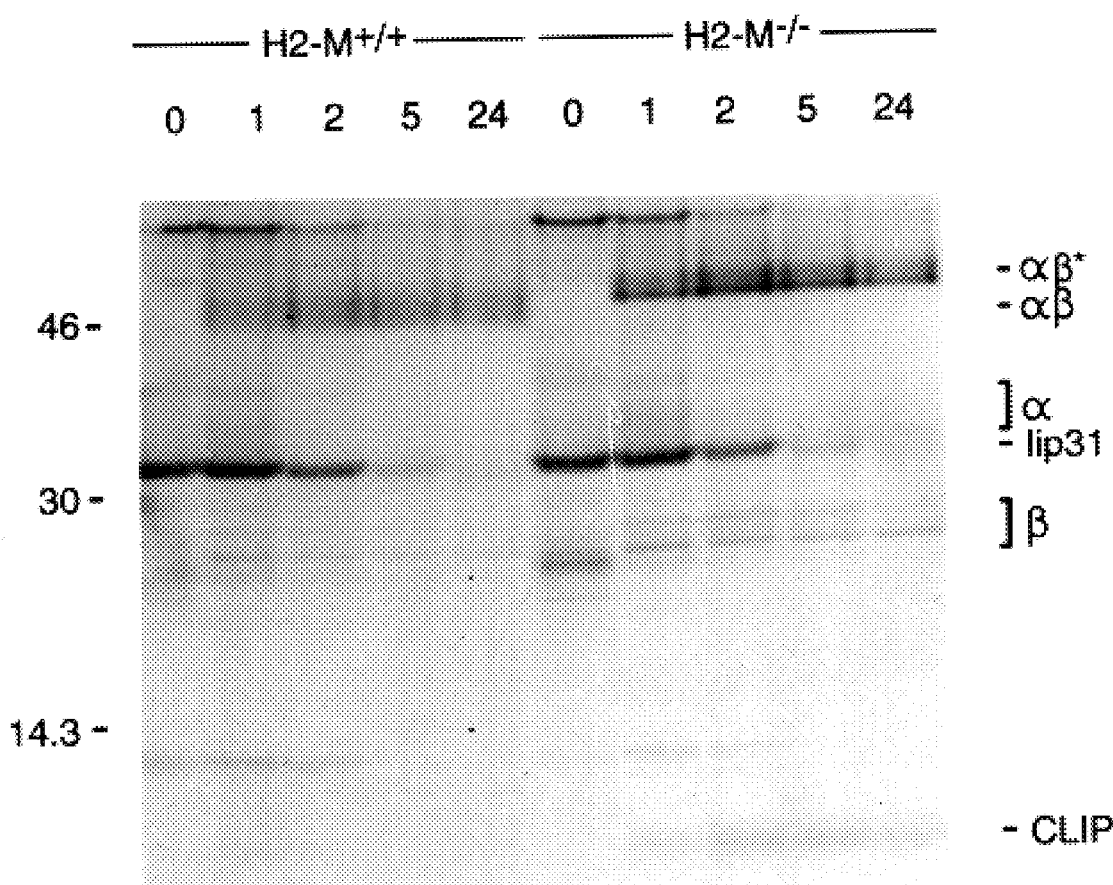
Figure 2D:
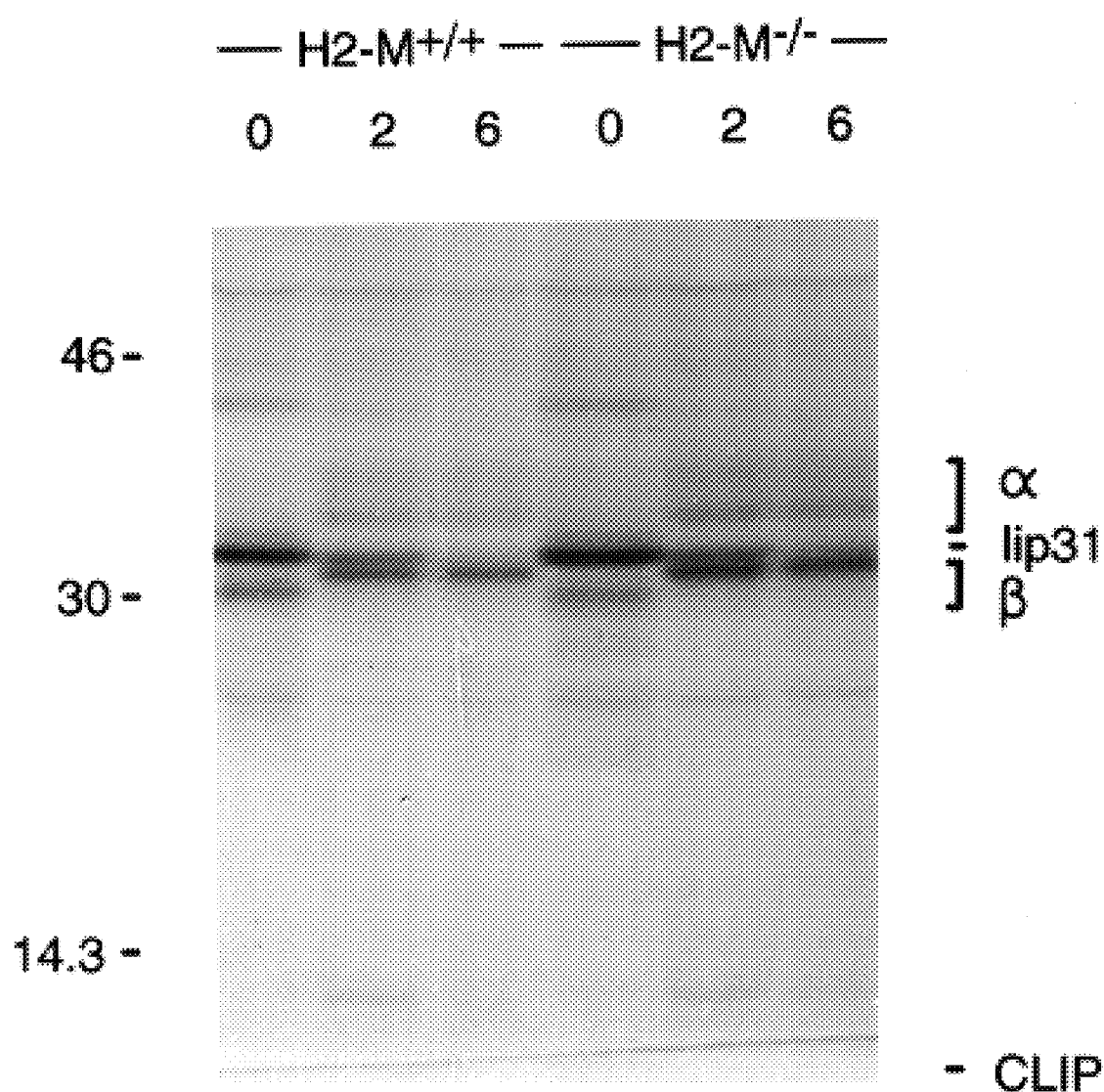

Under mildly denaturing conditions, class II molecules containing well-fitting peptides often migrate as dimers in SDS-PAGE gels (Stem and Wiley. 1992, Cell 68, 465. Sadegh-Nasseriand Germian, 1991, Nature 353, 167. Nelson et al., 1994, Nature 371, 250), whereas class II molecules with poorly fitting peptides dissociate and migrate as single $\alpha$ and $\beta$ chains. The SDS-stability of H2-$A^b$ molecules from wild-type or mutant mice was analyzed in a pulse chase experiment. After immunoprecipitation with M5/i 14, samples were analyzed by SDS-PAGE without boiling, thus leaving stable class II dimers intact. FIG. 2C shows that in splenocytes from H2-M+/+ mice, SDS-stable dimers ($\alpha\beta$) were formed within one hour of chase and were prominent also after 24 hours of chase. Only small amounts of SDS-unstable class II monomers were seen. Surprisingly, the H2-$A^b$ molecules precipitated from H2-M−/− splenocytes also migrated as SDS-stable dimers, though their migration was slightly slower than the migration of dimers derived from wild-type cells (FIG. 1C, $\alpha\beta$*). Some class II monomers were also seen and in addition, a low molecular weight band representing CLIP was prominent. H2-M−/−-derived H2-$A^b$ molecules appeared compact rather than floppy in nature (Viville et al., 1993, Cell 72, 635. Bikoff et al., 1993, J.Exp.Med. 177, 1699. Dommair et al., 1989, Cold spring Harbor Symp. Quant. Biol. 54, 409) migrating as distinct bands in contrast to the diffuse dimer band seen in the wild-type precipitate. These results suggests that a limited number of peptides, most likely CLIP, was responsible for the dimer bands. SDS-stable DR1-CLIP complexes have been reported (Bijlmakers et al., 1994, EMBO J. 13, 2699) and since CLIP binds strongly to H2-$A^b$ (Sette et al., 1995, J.Exp.Med. 181, 677) formation of SDS-stable dimers is conceivable, though unexpected. The intensity of the class II bands did not significantly decrease during the 24 hour chase period, indicating that the half-life of H2-$A^b$ in the mutant mice is similar to the half-life in wild-type mice. In boiled (and reduced) samples (FIG. 2D) the class II migrated as monomers and the only distinct difference between the wild-type and mutant precipitates was the large amount of CLIP present in the mutant sample. Immunoprecipitation with mAb In-1, which is reactive with the invariant chain (but not with CLIP), did not reveal any differences between mutant and wild-type cells in either boiled or nonboiled samples.

Figure 3A:
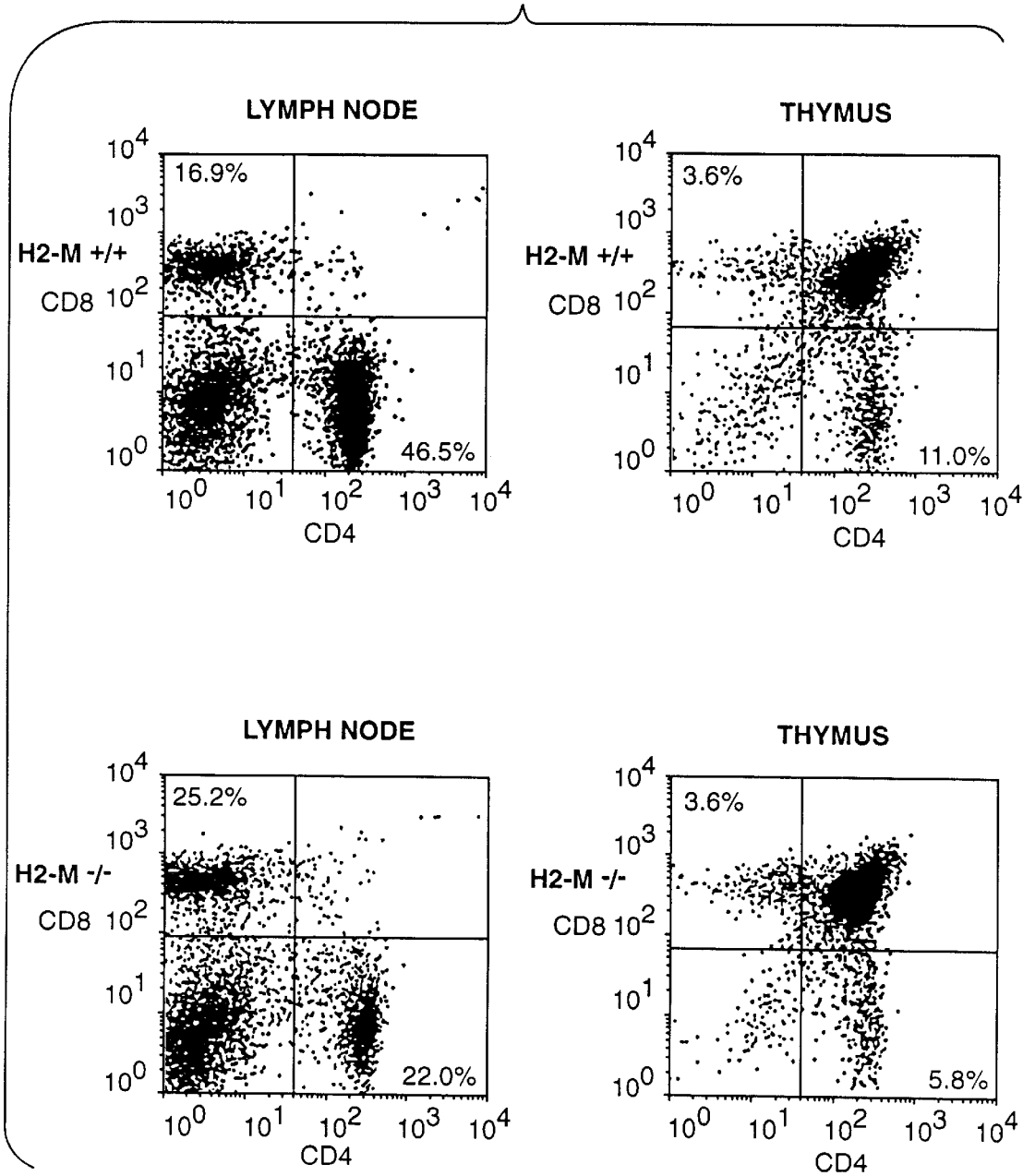
FIG. 3 Panels A, and B. Analysis of T cell markers in H2-M−/− and H2-M+/+ mice. (A) Lymph nodes cells or thymocytes were stained with antibodies reactive with CD4 and CD8 and analyzed by flow cytometry. (B) Analysis of lymph node CD4+ T cells for activation markers using CD45RB (left) and L-Selectin (right) indicated a naive phenotype. CD4$^+$ T cells from H2-M−/− snf H2-M +/+ mice were L-selectin$^{hi}$, CD44$^{lo}$, and CD45RB$^{hi}$, and few expressed markers associated with activation. For example, CD69 or interleukin 2 receptor.
Figure 3B:
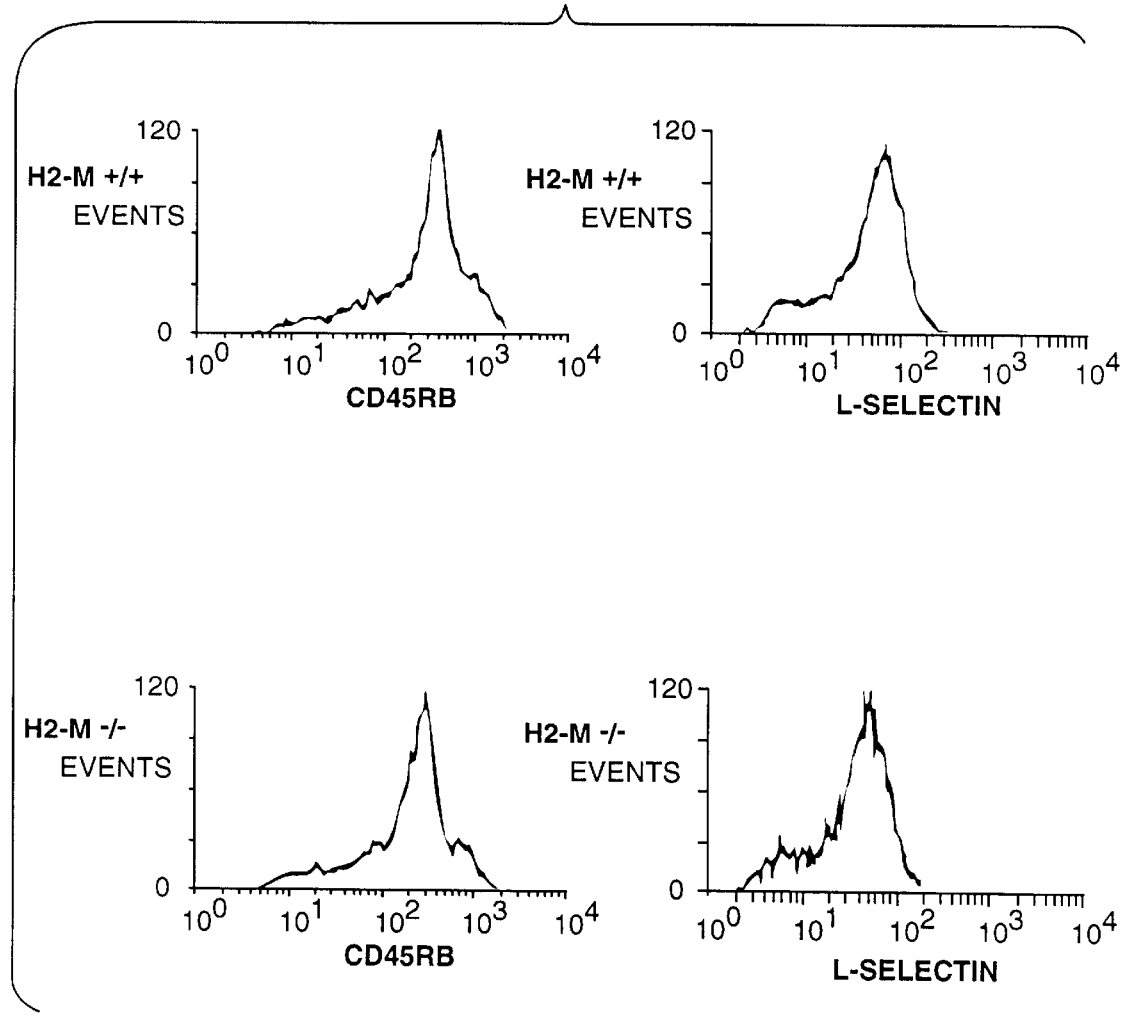

It was of interest to determine whether CLIP-associated class II molecules were able to mediate normal selection of CD4+ T cells. As illustrated in FIG. 3A, the proportion of lymph node (and splenic) CD4+ cells was reduced in H2-M−/− mice to approximately 30–50% of normal. This reduction in CD4+ cells was also seen in the thymus, though to a lesser extent. Nonetheless, the lymphoid tissues appeared normal and the finding that significant numbers of CD4+ cells did develop indicate that positive selection via H2-A$^b$ molecules did occur in the H2-M−/− mice. The phenotype of the CD4+ cells generated in these mice was similar to those from H2-M+/+ mice. Thus, the majority of extrathymic CD4+ cells displayed a naive phenotype (FIG. 3B) and analysis of Vβ usage suggested that the cells were polyclonal.

To determine whether the H2-M−/− CD4+ cells were functional, their ability to proliferate in response to alloantigens was analyzed. CD4+ cells from the mutant mice failed to respond to their own splenic APCs consistent with normal self tolerance induction. In contrast, these cells reacted strongly to APCs from MHC-matched wild type litter mates (and normal C57BL/6). This hyperreactivity was apparent as early as day 2 in culture and was maximal by day 3–4. Titration of responder CD4+cells indicated that the H2-M−/− cells were 10–100 fold more responsive to H2-A$^b$ than CD4+ cells from normal wild type mice. An abnormally strong proliferative response was also seen after exposure of H2-M−/− CD4+ cells to APCs from a variety of MHC-allogeneic strains, including B10.D2 (H2-A$^d$), B10.BR (H2-A$^k$) and B6.bm12 (H2-A$^{bm}$12). Not surprisingly, in view of the limited peptide repertoire of the H2-M−/− class II molecules, the APCs from H2-M−/− mice failed to stimulate MHC-allogeneic T cells (FIG. 4B). The inability to elicit proliferative T cell responses did not reflect poor costimulation since H2-M−/− APCs could provide normal costimulation for CD4+ cell responses to anti-CD3 antibody as well as to concanavalin A. Further, H2-M−/− APCs were not nonspecifically suppressive since the addition of these cells to cultures with normal APCs did not significantly alter the response.

These findings are consistent with the notion that a limited peptide repertoire (mainly consisting of CLIP) can support positive selection of significant numbers of functional CD4+ T cells. Nonetheless, the reduced number of CD4+ cells in these mice also argues that a normal density of class II molecules on thymic epithelial cells is not sufficient to achieve maximal levels of positive selection, but that peptide diversity contributes to the efficiency of this process.

The H2-M−/− mice do not display overt autoimmunity indicating that tolerance to CLIP-associated class II molecules is normal. The hyperreactivity of H2-M−/− CD4+ cells to H2-A$^b$ APCs from normal mice suggests, however, that the diversity of the class II-associated peptides is too limited in H2-M$^{-/-}$ mice to induce negative selection to self peptides other than CLIP.

The three-dimensional structure of HLA-DR3-CLIP (Ghosh et al., 1995, Nature 378, 457) suggests that class II-CLIP complexes may not be qualitatively different from other class II-peptide complexes. Therefore, the failure of allogeneic CD4+ T cells to respond to H2-M−/− APCs is unlikely to reflect a conformational change in the class II molecules which would abolish T cell receptor binding. The lack of response is more likely a reflection of the fact that most class II molecules on H2-M−/− APCs contain CLIP. Despite the high density of this complex on the H2-M−/− APCs the precursor frequency of T cells able to recognize a single class II-peptide complex (i.e. allogeneic MHC-CLIP) is presumably low and the reactivity of these cells undetectable in assays of proliferative response.

The data presented here show that H2-M is clearly essential for generating a normal repertoire of CD4+ T cells as well as for the presentation of a normal aray of peptide antigens.

What is claimed is:

1. A transgenic mouse whose somatic and germ cells comprise a disruption in the endogenous H2-Ma gene, wherein said disruption is generated by targeted replacement with a non-functional H2-Ma gene, and wherein said disruption results in CD4+ T cells from said mouse to have a greater proliferative response to antigen presenting cells from allogeneic mice as compared to the proliferative response of CD4+ T cells from wild-type H2-Ma mice to antigen presenting cells from allogeneic mice.

2. The mouse of claim 1, wherein said mouse is fertile and transmits the non-functional H2-Ma gene to its offspring.

3. The mouse of claim 1, wherein the non-functional H2-Ma gene has been introduced into an ancestor of the mouse at an embryonic stage by microinjection of the embryonic stem cells into mouse blastocyts.

4. The mouse of claim 1, wherein the non-functional H2-Ma gene has been introduced into the mouse at an embryonic stage either by microinjection of the embryonic stem cells into mouse blastocyts or coincubation of the embryonic stem cells with fertilized eggs or morulae.

5. The mouse of claim 1, which is designated as H2-M−/−.

6. A method for producing a transgenic mouse whose somatic and germ cells comprise a disruption in the endogenous H2-Ma gene, wherein said disruption is generated by targeted replacement with a non-functional H2-Ma gene, said method comprising:

(a) introducing an H2-Ma targeting construct comprising a selectable marker sequence into a mouse embryonic stem cell;

(b) introducing said mouse embryonic stem cell into a mouse blastocyst;

(c) transplanting said blastocyst into a recipient mouse;

(d) allowing said blastocyst to develop to term;

(e) identifying a transgenic mouse whose genome comprises a disruption of the endogenous H2-Ma gene in at least one allele; and (f) breeding the transgenic mouse of step (e) to obtain a transgenic mouse whose genome comprises a homozygous disruption of the endogenous H2-Ma gene, wherein said disruption results in CD4+ T cells from said mouse to have a greater proliferative response to antigen presenting cells from allogeneic mice as compared to the proliferative response of CD4+ T cells from wild-type H2-Ma mice to antigen presenting cells from allogeneic mice.

7. The method of claim 6, wherein the introducing of step (a) is by microinjection.

8. A cell line isolated from the transgenic mouse of claim 1, wherein the cells of said cell line comprise a disruption in the endogenous H2-Ma gene, wherein said disruption is generated by targeted replacement with a non-functional H2-Ma gene.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: cDNA (iv) ANTI-SENSE: NO (xi) SEQUENCE DESCRIPTION: SEQ ID NO:1:

GGATTCCTGT CAGGAGTTTC AAAG    24

(2) INFORMATION FOR SEQ ID NO:2:

(i) SEQUENCE CHARACTERISTICS:
        (A) LENGTH: 23 base pairs
        (B) TYPE: nucleic acid
        (C) STRANDEDNESS: double
        (D) TOPOLOGY: linear

```
        (ii) MOLECULE TYPE: cDNA (iv) ANTI-SENSE: NO (xi) SEQUENCE DESCRIPTION: SEQ ID NO:2:

AAGCGCATGC TCCAGACTGC CTT                                                         23

(2) INFORMATION FOR SEQ ID NO:3:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: cDNA (iv) ANTI-SENSE: NO (xi) SEQUENCE DESCRIPTION: SEQ ID NO:3:

GCCAAGTTCT AATTCCATCA G                                                           21

(2) INFORMATION FOR SEQ ID NO:4:

(i) SEQUENCE CHARACTERISTICS:
            (A) LENGTH: 36 base pairs
            (B) TYPE: nucleic acid
            (C) STRANDEDNESS: double
            (D) TOPOLOGY: linear (ii) MOLECULE TYPE: cDNA (iv) ANTI-SENSE: NO (xi) SEQUENCE DESCRIPTION: SEQ ID NO:4:

CCAGTTCTGT CAGCACAAGG TCTGGAGTGT TTAGGT                                            36
```